(12) United States Patent
Lipshaw et al.

(10) Patent No.: US 7,329,232 B2
(45) Date of Patent: Feb. 12, 2008

(54) LIMB ENCIRCLING THERAPEUTIC COMPRESSION DEVICE

(75) Inventors: Moses A. Lipshaw, San Diego, CA (US); Sandra Anne Shaw, Coronado, CA (US); Todd Alan Carpenter, San Diego, CA (US)

(73) Assignee: Circaid Medical Products, Inc., San Diego, CA (US)

( * ) Notice: Subject to any disclaimer, the term of this patent is extended or adjusted under 35 U.S.C. 154(b) by 32 days.

(21) Appl. No.: 10/789,065

(22) Filed: Feb. 27, 2004

(65) Prior Publication Data

US 2005/0192524 A1    Sep. 1, 2005

(51) Int. Cl.
*A61F 13/00* (2006.01)
*A61G 15/00* (2006.01)
*A41D 13/015* (2006.01)
*A61M 35/00* (2006.01)

(52) U.S. Cl. ............... 602/61; 128/845; 602/60; 2/455; 604/289

(58) Field of Classification Search ............ 602/77, 602/60–63, 20, 23, 26, 66; 606/201, 203; 128/869, 876–878, 882; D24/190
See application file for complete search history.

(56) References Cited

U.S. PATENT DOCUMENTS

| | | | | |
|---|---|---|---|---|
| 3,613,679 A | * | 10/1971 | Bijou | 602/75 |
| 3,667,462 A | | 6/1972 | Moon | |
| 3,831,467 A | * | 8/1974 | Moore | 602/26 |
| 3,853,123 A | * | 12/1974 | Moore | 602/26 |
| 3,856,008 A | * | 12/1974 | Fowler et al. | 602/62 |
| D234,271 S | * | 2/1975 | Moore | D24/190 |
| 3,935,858 A | * | 2/1976 | Harroff | 602/26 |
| 4,013,070 A | * | 3/1977 | Harroff | 602/21 |
| 4,090,508 A | * | 5/1978 | Gaylord, Jr. | 602/26 |
| 4,215,687 A | * | 8/1980 | Shaw | 602/60 |
| 4,379,463 A | * | 4/1983 | Meier et al. | 602/16 |
| 4,388,920 A | * | 6/1983 | Hajost et al. | 602/16 |
| 4,407,276 A | * | 10/1983 | Bledsoe | 602/16 |
| 4,441,493 A | | 4/1984 | Nirschl | |
| D278,083 S | * | 3/1985 | Meier | D24/190 |
| 4,597,384 A | | 7/1986 | Whitney | |
| 5,107,827 A | | 4/1992 | Boyd | |
| 5,146,932 A | | 9/1992 | McCabe | |
| 5,195,950 A | * | 3/1993 | Delannoy | 602/75 |
| 5,254,122 A | | 10/1993 | Shaw | |
| 5,472,414 A | | 12/1995 | Detty | |
| 5,513,658 A | | 5/1996 | Goseki | |
| 5,520,630 A | * | 5/1996 | Daneshvar | 602/60 |
| 5,626,556 A | | 5/1997 | Tobler et al. | |
| 5,628,725 A | | 5/1997 | Ostergard | |
| 5,653,244 A | * | 8/1997 | Shaw | 128/882 |
| 5,728,059 A | | 3/1998 | Wiesemann et al. | |
| 5,871,458 A | | 2/1999 | Detty | |
| 5,904,145 A | | 5/1999 | Reid | |
| 5,916,183 A | | 6/1999 | Reid | |
| 5,976,099 A | | 11/1999 | Kellogg | |

(Continued)

*Primary Examiner*—Patricia Bianco
*Assistant Examiner*—Tarla Patel
(74) *Attorney, Agent, or Firm*—Gordon & Rees, LLP

(57) ABSTRACT

A therapeutic compression garment made of flexible, foldable, light weight Velcro-type loop fabric having a central region for wrapping partially around a body part and a plurality of bands integrally connected to the central region and extending outwardly in opposite directions from both sides of the central region to cross each other and encompass the body part.

8 Claims, 12 Drawing Sheets

U.S. PATENT DOCUMENTS

| | | | |
|---|---|---|---|
| 5,993,405 A * | 11/1999 | Wynn | 602/62 |
| 6,050,967 A * | 4/2000 | Walker et al. | 602/75 |
| 6,101,629 A | 8/2000 | Colling | |
| 6,109,267 A | 8/2000 | Shaw et al. | |
| 6,142,965 A * | 11/2000 | Mathewson | 602/62 |
| 6,190,344 B1 | 2/2001 | Bobroff | |
| 6,196,231 B1 | 3/2001 | Reid | |
| 6,338,723 B1 * | 1/2002 | Carpenter et al. | 602/75 |
| 6,402,712 B1 | 6/2002 | Gauvry | |
| 6,425,876 B1 * | 7/2002 | Frangi et al. | 602/60 |
| 6,516,804 B1 | 2/2003 | Hoffman | |
| 6,545,193 B1 | 4/2003 | Morgenstern | |
| 6,656,141 B1 | 12/2003 | Reid | |
| 2003/0171706 A1 | 9/2003 | Nelson | |
| 2004/0111047 A1 | 6/2004 | Reid | |

\* cited by examiner

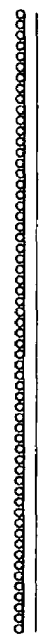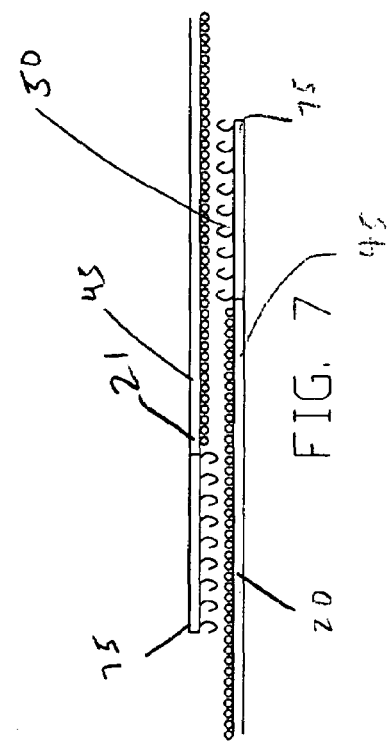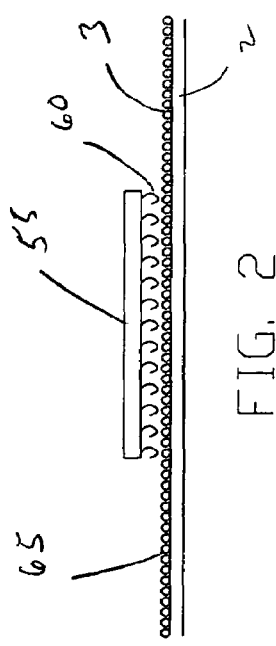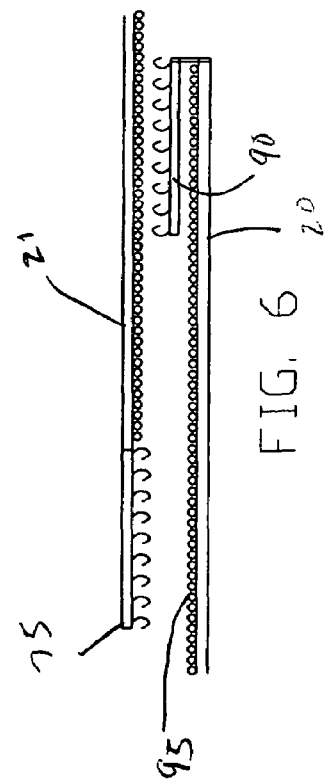

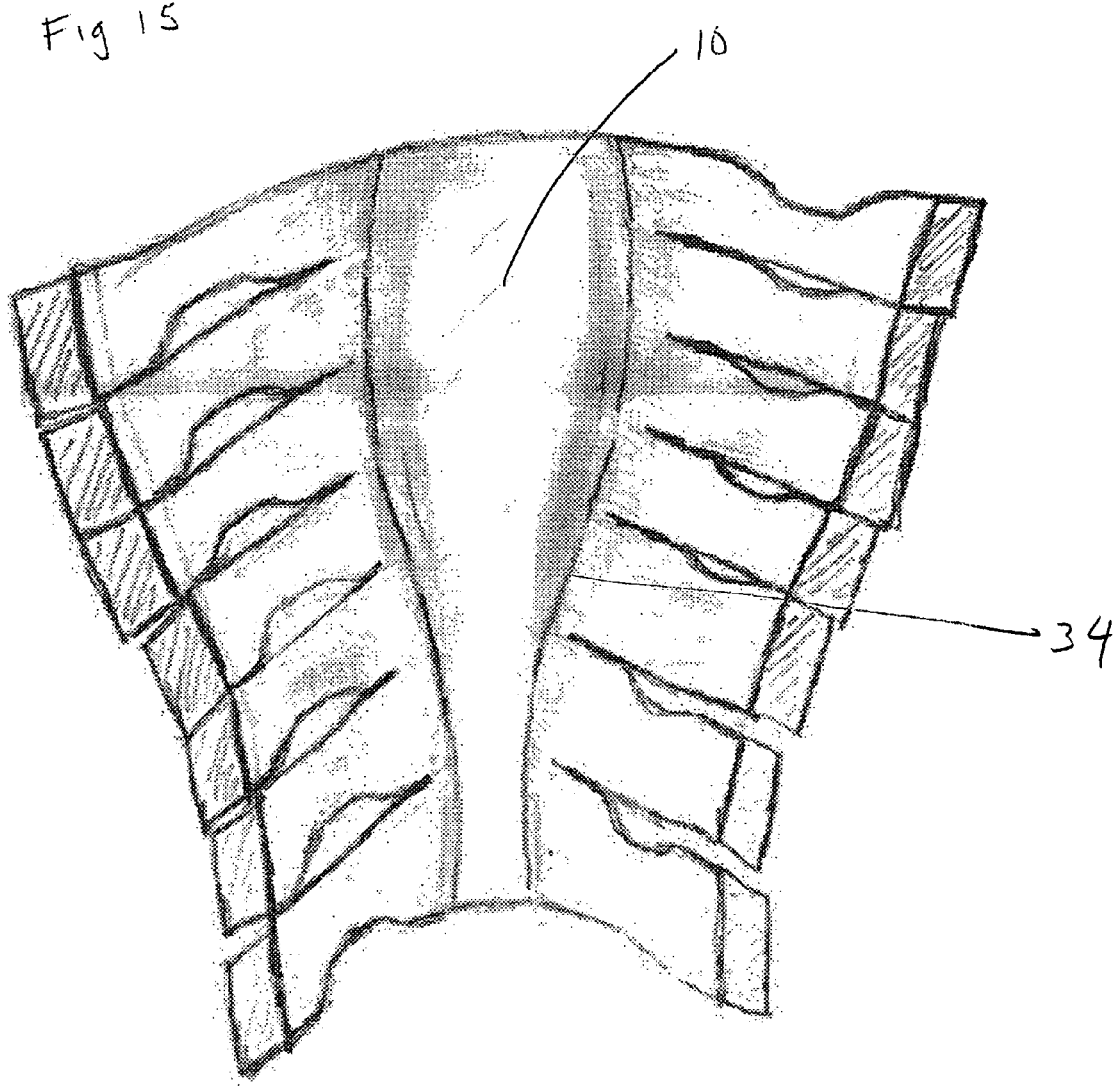

LIMB ENCIRCLING THERAPEUTIC COMPRESSION DEVICE

BACKGROUND OF THE INVENTION

This invention relates to devices for applying compression to parts of the body for therapeutic reasons.

Compression applied to a body part, such as a limb, is essential for resolving many circulatory disorders. The application of compression at the appropriate level has therapeutic benefits. For example, it restores circulation, relieves swelling, treats pain, heals ulcers, and treats varicose veins.

Elastic and inelastic garments have been employed in compression therapy of the limbs. Most of these garments suffer various degrees of shortcomings, particularly discomfort, loss of compression, difficulties in application and removal, lack of adjustability, and ineffectiveness.

A desirable trait of compression devices is that they provide to the limb compression levels that are dynamic, fluctuating in response to short-term changes inside the body part. Compression requirements change as internal pressures change, depending on whether the patient is upright or prone. Furthermore, the movement of fluid out of a body part is facilitated by the pumping effect caused by fluctuations in pressures. Such pressure fluctuations can be enhanced by compression devices that resist changes in limb size, such as those that occur during muscle flexion.

Patients have observed that stockings, wraps, and bandaging systems made entirely of elastic materials are uncomfortable. Fully elastic devices deliver an unchanging level of pressure, which alternately feels either "too tight" or "too loose" to the patient depending on the patient's position. These elastic systems also do not resist small changes in limb circumference, and hence do not provide the fluctuating pressures that are needed to assist with pumping fluid out of the body part.

To be effective, compression devices need to maintain appropriate compression over time. Large changes can occur in limb volume, reflecting either diurnal fluctuations or progressive changes in the degree of swelling. Devices that provide compression through the wrapping of materials with limited elasticity, such as with the Unna's boot, cannot accommodate such changes in limb volume. For example, they may initially provide appropriate compression, which is dynamic in response to internal changes, but after hours of use the movement of fluid out of the limb will result in an overall loss of pressure. And because these systems are wrapped around the limb in layers, it is not practical to periodically remove and re-apply the wrapping at the appropriate compression level.

In the case of more elastic systems, such as long-stretch bandages and elastic stockings, the greater elasticity helps them to sustain consistent compression levels over time. However, if changes in limb volume are great enough, pressures under the devices can go outside the appropriate therapeutic range. An additional problem with elastic stockings is that if they are sized incorrectly, or if the body part is of an irregular shape, the pressure could be incorrect under all or part of the garment from the onset. In the case of elastic bandages, it is easy to apply the layers at too high or low of a pressure, requiring a time-consuming removal and re-application.

A useful trait of compression garments is that they be easy to apply and adjust. This helps to ensure appropriate, sustained compression levels by allowing the user to adjust to accommodate changes in limb volume, and enabling the garment to be adjusted to an exact fit regardless of limb shape. Being easy to apply also increases the likelihood that the patient will continue to use the device and obtain its therapeutic benefits. Stockings can not be adjusted and are difficult to slide onto the limb. Bandaging systems can not be adjusted without being removed completely, and require skill for proper application.

Devices such as described in U.S. Pat. No. 5,653,244 are primarily inelastic, and can be adjusted through series of interlocking bands. As such they provide dynamic compression that can be sustained over time. However, because they are primarily inelastic, compression levels quickly go down with changes in volume, so sustaining compression requires frequent re-adjustment of the bands. Another consequence of being primarily inelastic is that it is more difficult to hold force in the bands while applying, and as a consequence, more effort is required by the user during application—either in the form of greater force, or the use of a greater number of bands on the garment. Furthermore, because the pairs of bands interlock—one member of a pair of bands passes through a hole in the other member—they require a certain amount of manual dexterity to apply. This is particularly disadvantageous, as many users are older or have other limitations of mobility.

Compression devices are therefore needed that are easy to apply, and that provide compression that is both sustained (in that significant long-term changes in limb volume can be accommodated), and dynamic (such that short-term changes to internal pressure can be countered). To this end, compression devices are needed that provide the ability to apply and adjust compression as quickly and easily as possible. Compression devices are also needed that are inelastic enough to provide compression levels that respond dynamically to changes in patients' compression requirements, while still being elastic enough so that the device does not readily loose appropriate compression. A need also exists for compression devices that can be applied to parts of the body that have varying circumference and that are comfortable to wear throughout the day and in different postures.

Sustained yet dynamic compression is key to proper treatment. It is often a problem with compression devices that the applied compression goes down over time or with changes in limb volume. It is often a problem with other devices that in order to sustain compression, the device must be so elastic that compression levels do not fluctuate with changes in patient need. Providing compression that has a low but significant level of elasticity, and having a means of easily adjusting compression levels, enables sustained and dynamic compression levels to be maintained.

U.S. Pat. No. 3,845,769 relates to a boot having a split sleeve of essentially unyielding material shaped to fit a leg. The sleeve is held in position and compression is applied by a plurality of bands of interlocking fabric material, such as Velcro or Scotchmate.

U.S. Pat. No. 4,215,687 relates to a combination or kit, which permits the in situ construction and assembly of a therapeutic compression device directly on the patient by a doctor or other skilled person. The combination or kit includes a Velcro-type anchoring tape having an interlocking fabric material on one side and a plurality of body or limb encircling Velcro-type bands which are assembled, one by one, in edge-to-edge relationship either by direct contact with the anchoring tape or by indirect contact through Velcro-type splicing means. These custom-made therapeutic compression devices have achieved wide recognition in healing leg ulcers and in the treatment of lymph edema. On the other hand, the custom construction which requires splicing of the body or limb encircling bands when they are too long and when the portion of the body or limb is contoured is a tedious and time consuming task.

U.S. Pat. No. 5,120,300 relates to a compression band for use in the therapeutic device disclosed in U.S. Pat. No. 4,215,687 and, more particularly, to a compression band for quick and easy application to and removal from a body part.

U.S. Pat. No. 5,254,122 relates to a therapeutic compression device of the type disclosed in U.S. Pat. No. 4,215,687 which includes a longitudinally extending splicing band or slide fastener which facilitates quick and easy removal of the device from the body or limb and quick and easy reapplication to the body or limb without the necessity of unthreading the adjusted compression bands.

U.S. Pat. No. 5,653,244 relates to a therapeutic compression garment made of flexible, foldable, light weight Velcro-type loop fabric having a central region for wrapping partially around a body part and a plurality of pairs of bands integrally connected to the central region and extending outwardly in opposite directions from both sides of the central region to encompass the body part. One of the bands of each pair has a slot to accommodate the opposite band in threaded, folded relationship.

U.S. Pat. Nos. 5,918,602 and 5,906,206 relate to the therapeutic garment disclosed in U.S. Pat. No. 5,653,244 and adapted for the leg in combination with an ankle-foot wrap for applying therapeutic compression to the leg, ankle and foot.

U.S. Pat. No. 6,338,723 relates to a device for compression of objects such as parts of the body. The device has the form of a band sized to encircle the compressible object and having a component or components made of an elastic material. Indicia are printed on the device such that the stretch of the elastic material as the device is tensioned around the body part causes increased separation of the indicia or movement of a free end of the band with respect to the indicia. A system measures the separation of the indicia and converts it to compression as a function of the circumference of the body part.

SUMMARY OF THE INVENTION

The present invention is a garment for applying compression to a limb. The garment, which has inner and outer surfaces, comprises a central region of substantially inelastic material. Lateral regions are disposed on opposite sides of the central region. A plurality of bands extends from the opposite lateral regions. Each band comprises a distal region, proximal and distal edges, inner and outer surfaces, and a fastener for detachably securing the distal region to a band extending from the opposite lateral region or to the opposite lateral or central region. In use, the user encircles the limb, the inner surface of the garment placed against the limb, and draws the first lateral region toward the second longitudinal edge to stretch the central region and thereby provide a tension in the garment that will compress the limb.

Preferred embodiments of the garment involve the central and lateral regions which are biased into a three-dimensional curvature in order to fit the body part.

Various embodiments are provided in which the opposing bands extend either substantially perpendicular to a longitudinal axis of the central region, and the proximal and distal edges are substantially parallel to each other; or the bands extend from a lateral region at an angle with respect to a longitudinal axis of the central region; or combinations thereof. For example, an embodiment provides at least one set of opposing bands extends substantially perpendicular to a longitudinal axis of said central region, and at least one set of opposing bands extends at a non-normal angle to the longitudinal axis of the central region.

Still other embodiments provide bands in which recesses are formed in either the proximal or distal edges of the bands to facilitate wrapping engagement by juxtaposition of the proximal and distal recessional edges of opposing bands.

Other embodiments provide garments which bear an indicia system for measuring the compression which the garment applies to the limb. A preferred embodiment provides a card having a scale for measuring the separation of the position of the at least one indicia from the reference position. Reading the card in relation to the indicia system indicates the compression level for the pre-measured circumference of the body part, thereby permitting the user to determine the actual compression provided by the garment and to adjust the compression provided by the garment accordingly.

The garment has an embodiment which comprises a pocket attached adjacent the distal end of a band. The pocket is sized to admit at least one finger inserted through an opening in the pocket that faces in a direction substantially away from the distal end of the band. The user can urge the end of the band around the body part by inserting at least one finger through the opening into the compartment of the pocket and pushing or pulling with the at least one finger toward the opposite side of the garment.

In another aspect, the invention provides a method for applying therapeutic compression to a body part for treating a medical disorder which requires compression therapy. The method involves the step of applying with sufficient pressure to said body part a garment of the invention for a sufficient period of time to mitigate swelling in the limb. The method is suitable for treating medical disorders such as lymphedema, phlebitis, varicose veins, stasis ulcers, obesity, circulatory disorders; and for treating swelling due to traumas such as post-fracture edema, injury edema, and post-burn therapy.

OBJECTS OF THE INVENTION

An object of the present invention therefore is to provide a substantially non-elastic therapeutic compression garment allowing the user to more easily apply the garment without threading or interlocking all of the bands.

Another object of the present invention therefore is to provide a therapeutic compression garment of simpler design so labor and material costs are significantly reduced.

Yet another object of the present invention is to provide a therapeutic compression garment with a smoother more conforming fit by incorporating slightly elastic materials.

Another object of the present invention is to provide a therapeutic compression garment that is comfortable to wear.

Yet another object of the present invention is to provide a therapeutic compression garment, which by providing a slightly greater resting pressure through use of elastic materials or through the use of curved limb-shape accommodating seams, does not slide on the limb.

Still another object of the invention is to provide a therapeutic compression garment that provides effective treatment.

Another object of the invention is to provide a therapeutic compression garment that will provide a distal-proximal compression gradient along the body part.

Yet another object of the invention is to provide a therapeutic compression garment that allows the user to quickly adjust compression levels without having to remove the garment from the limb.

Still another object of the invention is to provide a therapeutic compression garment that is easy to tighten when setting the compression.

Another object of the invention is to provide a therapeutic compression garment that is constructed to match the contour of the limb.

Yet another object of the invention is to provide a therapeutic compression garment that, depending on the materials, can be fabricated for short or long-term use.

Still another object of the invention is to provide a therapeutic compression garment with a minimal number of bands for ease of application.

Other objects, features, and advantages of the present invention will become more fully apparent from the following detailed description of preferred embodiments, the appended claims, and the accompanying drawings in which:

DESCRIPTION OF THE DRAWINGS

FIG. 2 is a sectional view taken along line 2-2 of FIG. 1 looking in the direction of the arrows;

FIG. 4 is a sectional view taken along line 3-3 of FIG. 3 looking in the direction of the arrows;

FIG. 6 is a sectional view taken along line 4-4 and 5-5 of FIG. 5 when the bands are wrappingly engaged around the limb looking in the direction of the arrows;

FIG. 7 is a sectional view taken along line 6-6 and 7-7 of FIG. 5 when the bands are wrappingly engaged around the limb looking in the direction of the arrows;

FIG. 15 is an assemblage of the central region, lateral regions and bands shown in FIG. 8.

DETAILED DESCRIPTION OF THE PREFERRED EMBODIMENTS

Figure 1:
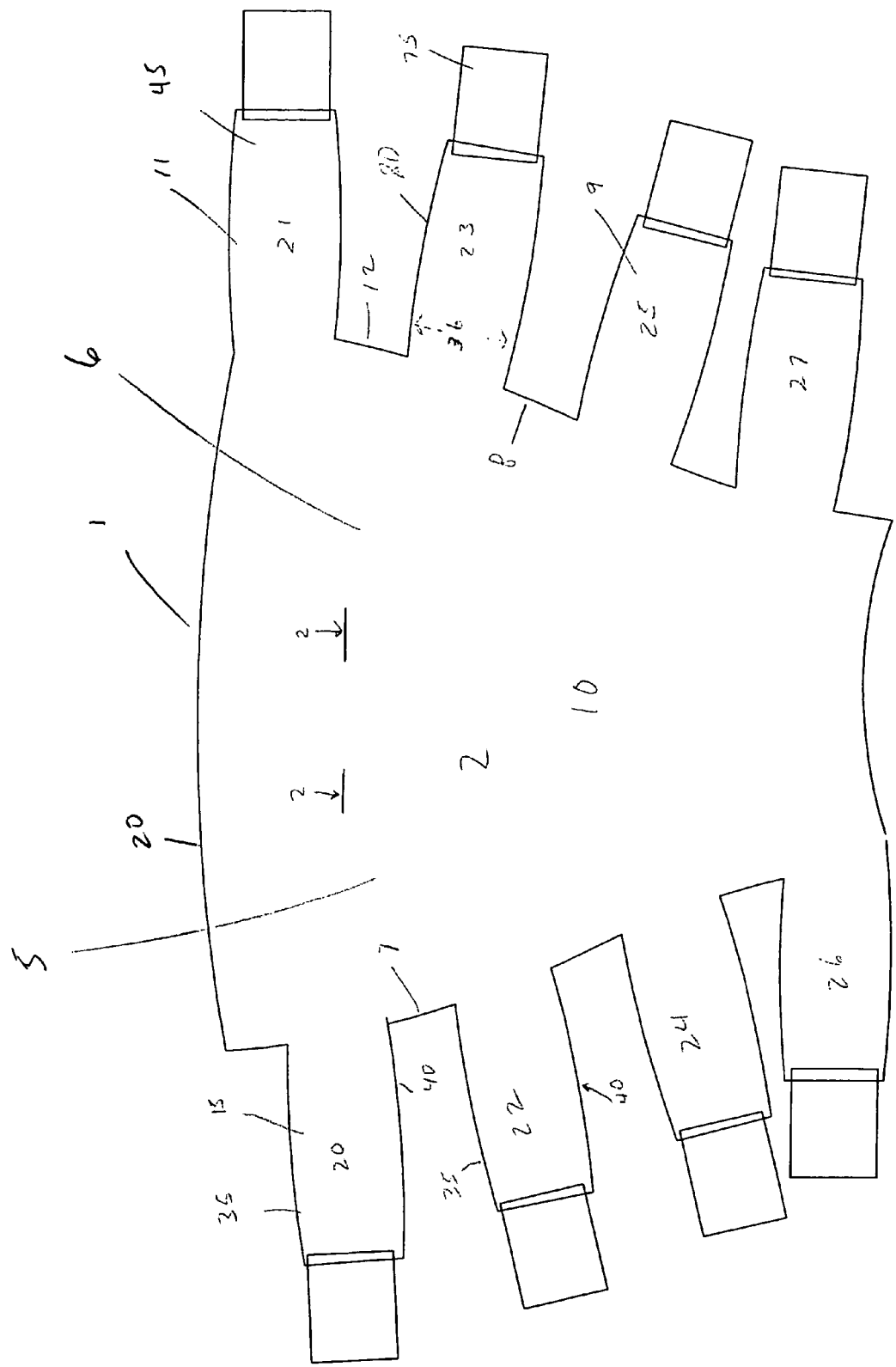
FIG. 1 is a view of the inner surface of a therapeutic compression garment of the present invention.

A preferred embodiment of the invention is shown in FIG. 1. The garment 1 has a central region 10 which has an inner surface 2 and an outer surface 3 (FIG. 2). The central region 10 is formed from material which is flexible and substantially inelastic. Lateral margins 7, 8 are disposed respectively in lateral regions 5, 6 which extend laterally from the central region. In practice, the central region is wrapped partially around a user's limb.

Extending from opposite lateral margins 7, 8 of the lateral regions 5, 6 are a plurality of bands (20-21, 22-23, 24-25, 26-27). Each band 15, which has an inner 9 and an outer surface, has a proximal edge 35 and a distal edge 40 and terminates in a distal region 45. The bands 15 are positioned for wrappingly or circumferentially engaging either with the opposite lateral region or with the edges and/or the surfaces of one or more bands extending from the opposite lateral margin.

Figure 8:
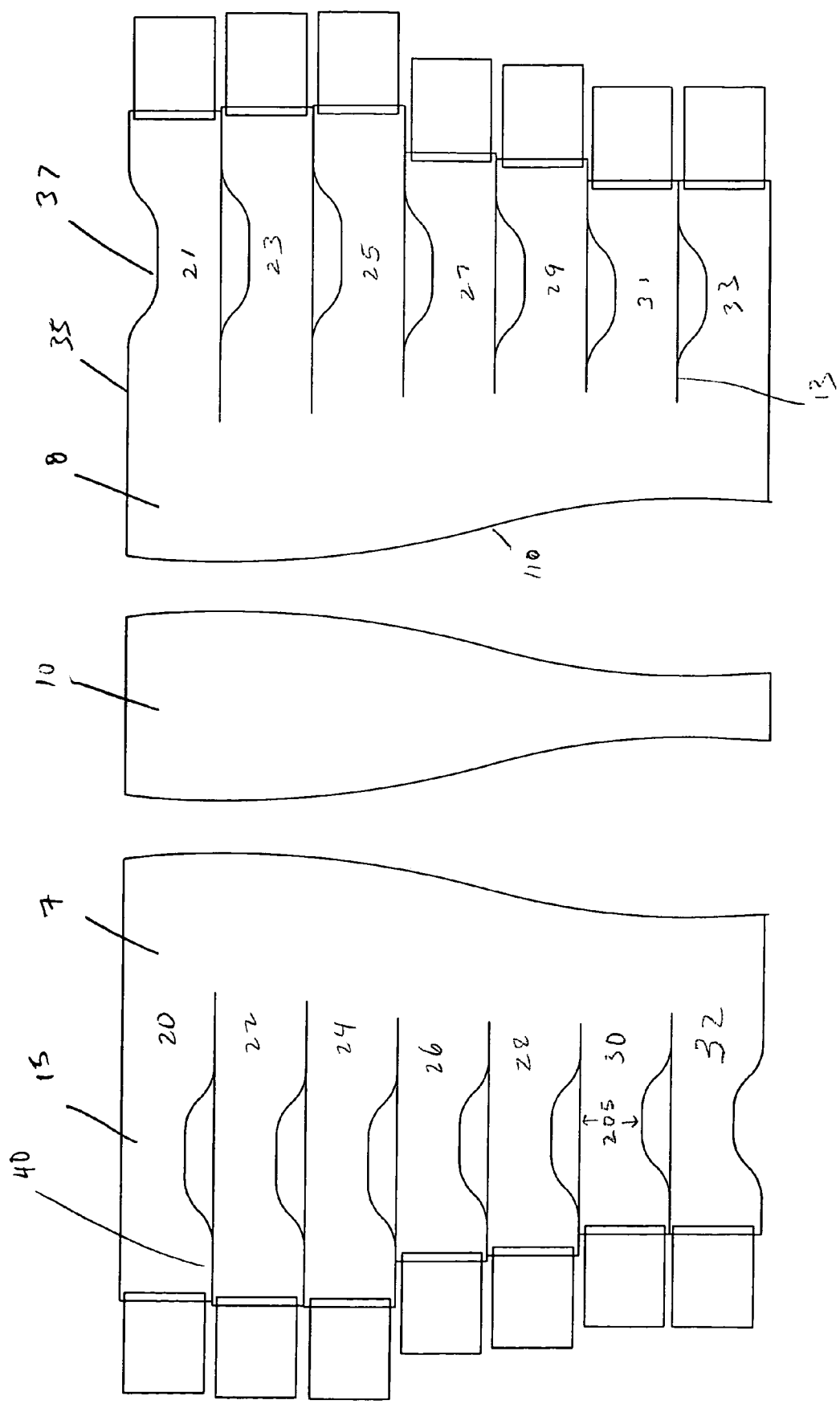
FIG. 8 is a view of the inner surface of another embodiment of the therapeutic compression garment of the present invention.
Figure 9:
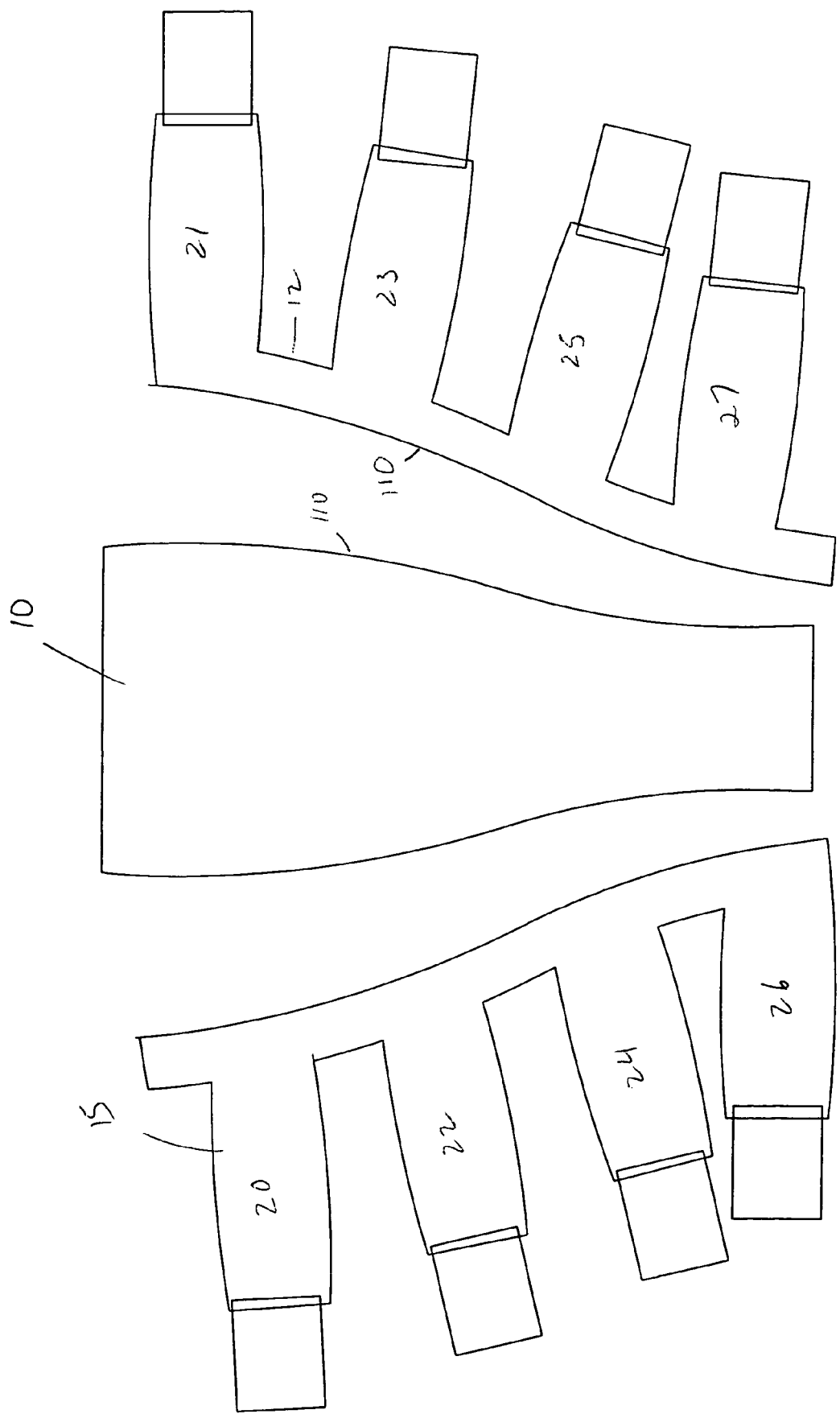
FIG. 9 is a view of the inner surface of another embodiment of the therapeutic compression garment of the present invention.

It should be understood that bands which extend from a lateral region, when wrapped circumferentially around the limb, engage surfaces and/or edges of one or more bands extending from the opposite lateral region. The term "opposing bands" refers to a set of bands which engage each other when wrapped. In some embodiments, a set of opposing bands comprise a pair of bands (FIG. 8). In other embodiments, a set of opposing bands comprises three bands, as shown in FIG. 9 in which, a set of opposing bands, when wrapped, involves bands 20 and 22 juxtaposingly engaged with band 23.

In certain devices, bands extend from the lateral regions at independent angles with respect to the longitudinal axis of the central region. Accordingly, a device may comprise sets of opposing bands which all extend perpendicularly from the longitudinal axis, or all extend at non-normal angles; or any combination of normal and non-normal angles. Furthermore, the bands of a set of opposing bands may extend at angles independently of each other.

Positioned on the distal region 45, integrally or detachably, of each band 15 is a fastener 75 which when circumferentially stretched about the limb detachably secures either to the outer or inner surface of a band extending from the opposite lateral margin, or to the outer or inner surface of the central region or lateral region 5 or 6 on the opposite side of the garment. In any case, a band 15, in wrapping engagement about the limb, detachably secures to an opposite lateral region and/or to an opposite band of the set of bands to which it belongs as it encircles the limb, drawing the first and second lateral regions toward each other, which tensions the central region, and thereby tensions the central region, thereby providing a tension in the garment that compresses the limb.

Figure 3:
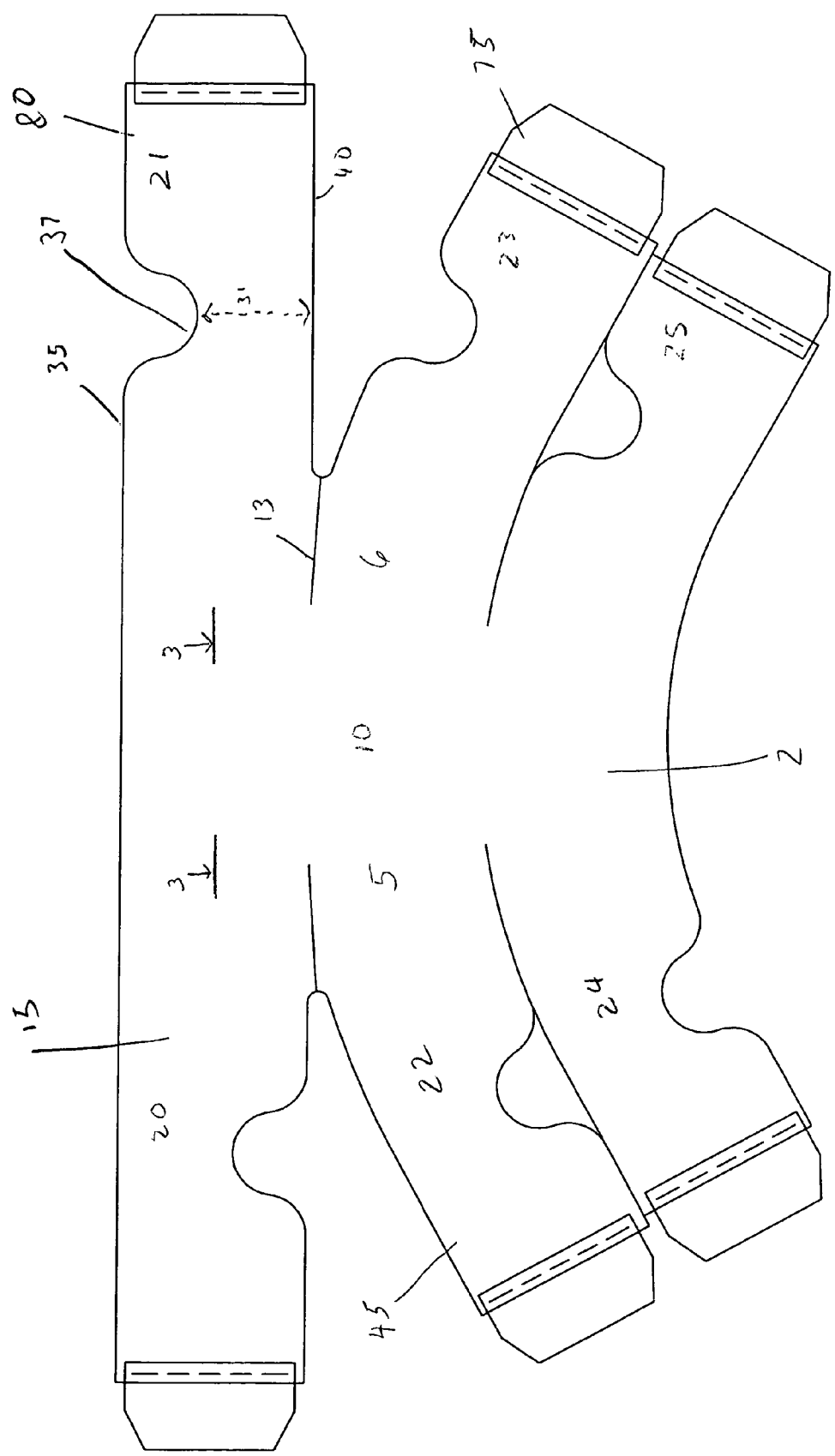
FIG. 3 is a view of the inner surface of another embodiment of the therapeutic compression garment of the present invention.
Figure 5:
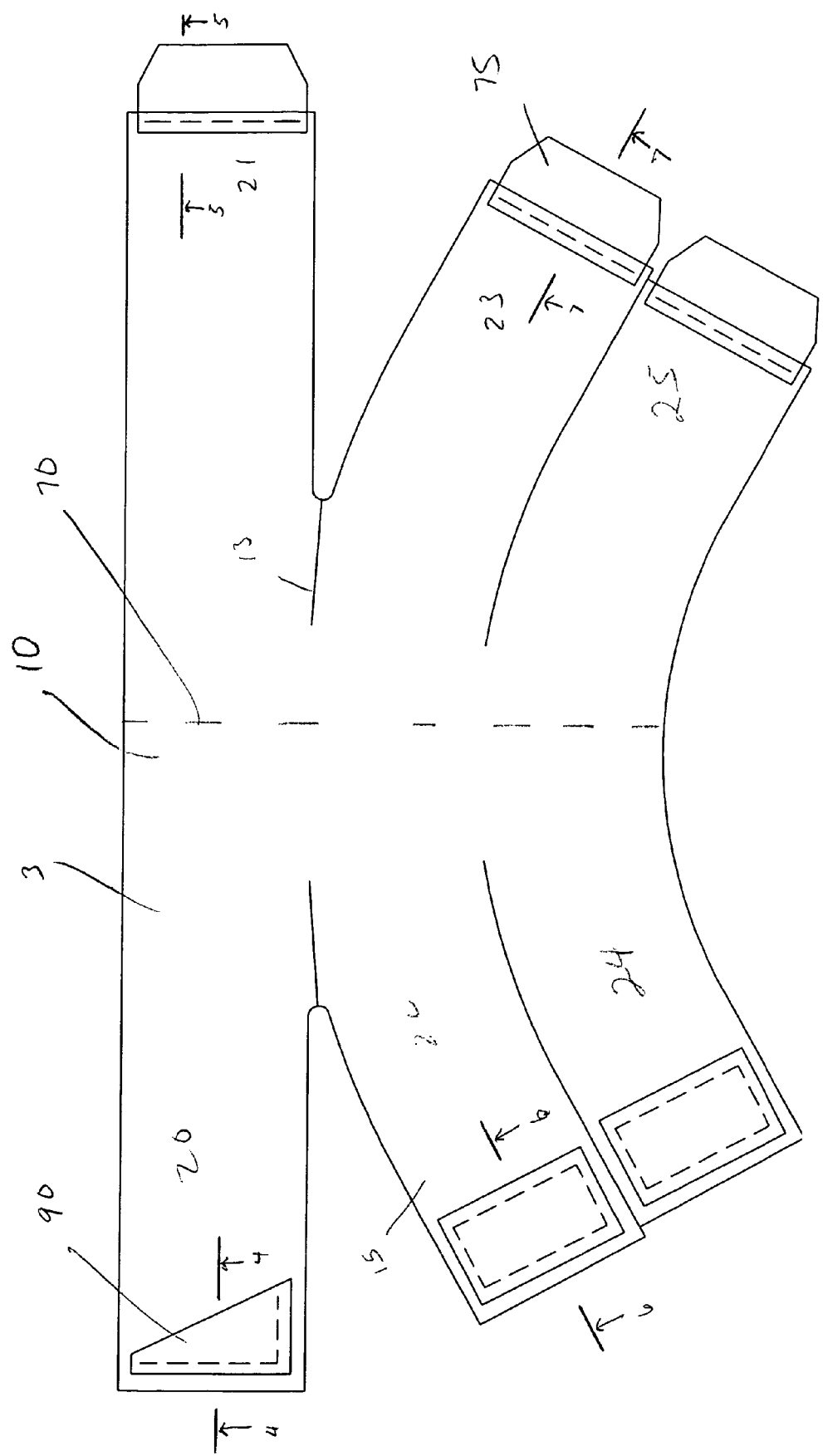
FIG. 5 is a view of the outer surface of another embodiment of the therapeutic compression garment of the present invention.

In one mode of fabrication, the therapeutic compression garments shown in FIG. 1, FIG. 3, and FIG. 5 are made in one piece from a flexible, foldable hook and loop type fabric (e.g. Velcro (tm)) having an outer loop surface which is preferably a light weight loop fabric of the type designated Velcro 3610 or Velcro 3800, the former being substantially inelastic and the latter having a limited stretch at least in the vertical or longitudinal direction. Other suitable materials range from inelastic to those with some elasticity such as neoprene that has a small amount of elasticity especially in the longitudinal but also circumferential axis.

Figure 10:
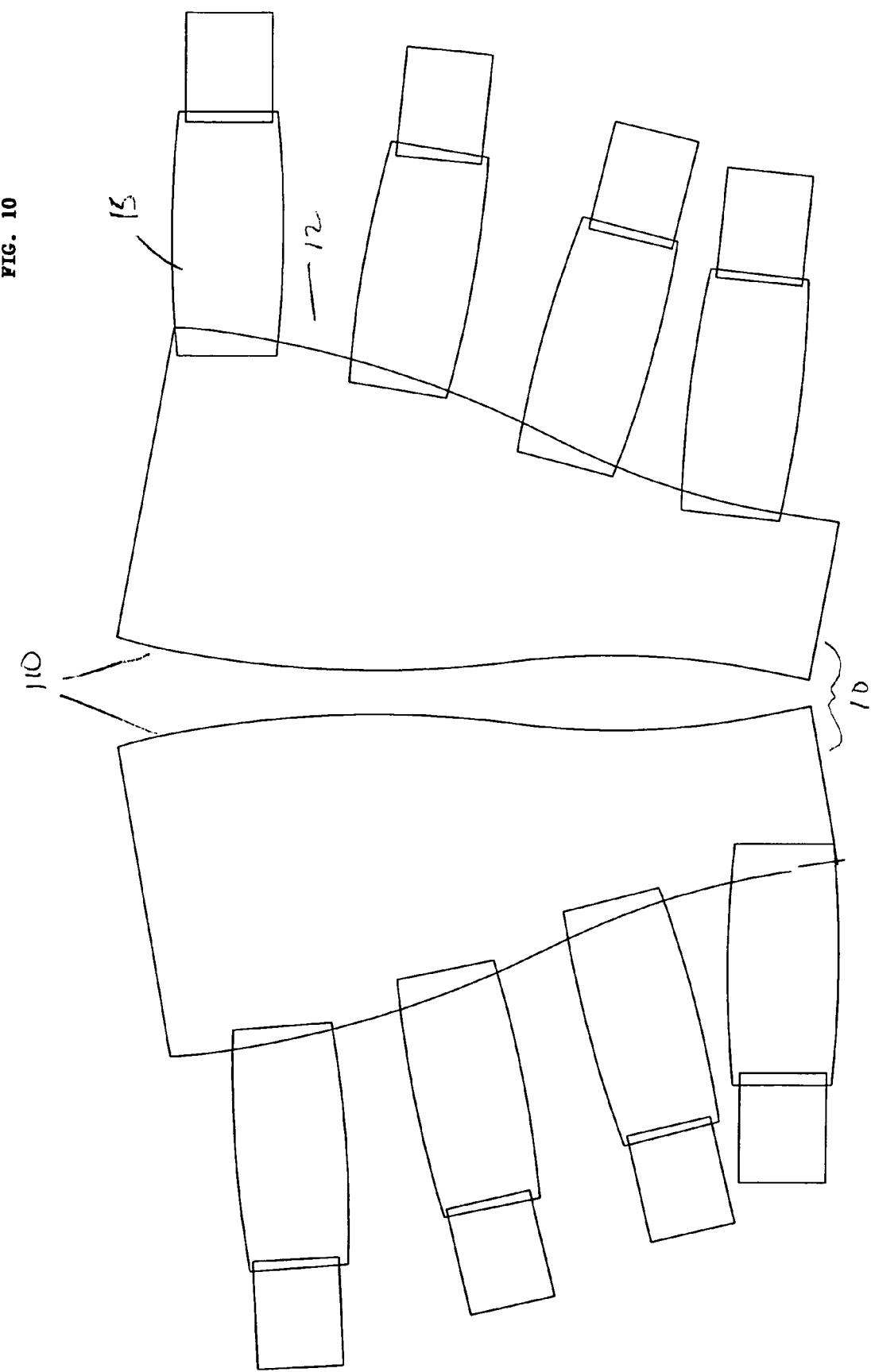
FIG. 10 is a view of the inner surface of another embodiment of the therapeutic compression garment of the present invention.

The central region 10 is wrapped partially around the body part. Bands extending from a lateral region are connected to bands extending from the opposite lateral regions and, prior to wrapping around the limb, extend outwardly in opposite directions. The bands 15 are separated or defined by spaces 12 or by slits 13. As illustrated in FIG. 1, FIGS. 3 and 5, variation in the space between bands generates different amounts of overlap between sets of bands, which extend from opposite lateral regions, when applied to the body part. In FIGS. 1, 9 and 10, band 20 opposes band 21. Bands 21 and 23 oppose band 20. Band 23 is opposed by bands 20 and 22; band 22 is opposed by bands 23 and 25, and soon. In FIGS. 3 and 5, there are three sets of opposing bands: 20-21; 22-23; and 24-25.

In FIG. 8, opposing bands are: 20-21; 22-23; 24-25; 26-27; 28-29; 30-31; 32-33.

In FIG. 1, the bands 15 wrappingly engage by encircling the limb so as to fit into an opposite space 12. For example, band 20 is wrapped into space 12 between bands 21 and 23 so that the proximal edge of band 20 is in juxtaposition with the distal edge of band 21; and the distal edge of band 20 juxtaposes the proximal edge of band 23.

Fasteners 75 made of hook material (such as that sold under the trademark Velcro) are attached to the unanchored ends, i.e. distal regions of the individual bands, and serve as means for detachably securing the band to loop-type material of the outer surface of the lateral region on the opposite side of the garment. The act of securing the distal regions of the bands to the opposite lateral regions serves to draw the first lateral region toward the second lateral region, which stretches the central region, thereby providing a tension in the garment that compresses the limb.

The bands are spaced and their extension from the lateral region angled in a manner to accommodate opposing bands in crossing and overlapping relationship, and wherein hook and loop type hook surface are positioned at the ends of the inner surfaces of at least half of the bands, whereby opposing bands can be extended toward each other with each band overlapping another and tightened to apply the desired compression and the inner hook surfaces can be pressed against the outer loop surface to anchor the bands in a tightened condition.

The width 36 of a band can be sized to account for the reduced surface area caused by necking that can occur when using an elastic material for the bands. When a band is stretched along it's longitudinal axis, the width of the band can narrow. For example, if the distal and/or proximal edges of overlapping bands are curved outward to compensate for necking, minimum overlap of bands occurs with this design but the body part or limb remains completely encompassed.

Referring to FIG. 3, the bands may include areas of reduced width 31 created by a recess formed into a proximal 35 or distal edge 40 of the band. When wrapped around the body part, the recessed areas of opposing bands accommodate each other in register, allowing the bands to overlap without bunching. These reduced widths 31 are positioned and sized to create various standard circumference sizes (i.e. small, medium, large) of the therapeutic garment. The "sizes" of circumference preferably correspond to ranges of circumferences. Devices for different body parts would require different ranges.

In alternative embodiments (all of the opposing bands in FIGS. 3, 5, and 8) some or all of the opposing bands are positioned to partially or completely overlap each other when wrappingly engaged. The inner surfaces at or near the distal ends 45 of the bands have hook-type surfaces 50 for detachable attachment to loop-type material positioned on the outer or inner surface of the opposing band or opposing lateral region.

An embodiment with both opposing bands having Velcro-type hook surfaces and the bands completely overlapping would require one set being on the inner surface and the other on the outer, where one set would attach to an inner loop surface of the garment and the other would attach to an outer loop surface. (FIG. 7 and bottom 2 pairs of bands in FIG. 5).

Pockets

Compression devices according to the present invention require the tightening of bands to establish tension in the material of the device along a circumference of the body part or limb. This requires pulling or pushing on tabs attached to the free ends of bands, i.e. distal ends of bands. The user has to grasp the free ends or tabs with his or her fingers and pull or push, which requires adequate finger dexterity and strength. Persons suffering from a circulatory disorder and possibly some other disability may have some difficulty pulling or pushing with the force necessary to achieve a good compression and retain their grip on the free end or tab.

Accordingly, the present invention provides a pocket 90 formed in the distal region of a band assisting the user to push or pull the free end of the band with his or her fingers. This pocket may be used with any of the compression devices shown and described in this specification.

Figure 11:
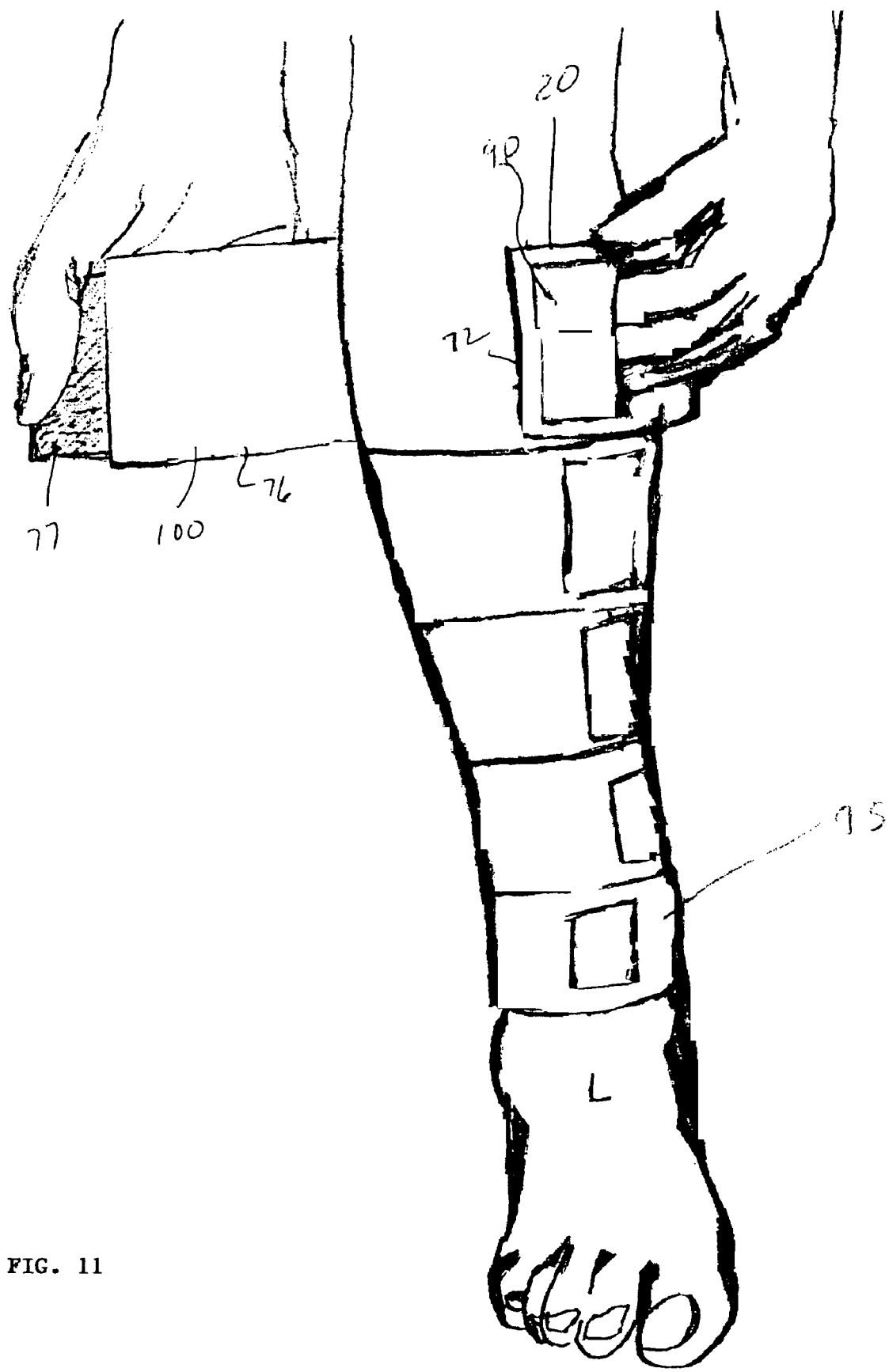
FIG. 11 is a perspective view of a garment similar to FIG. 5.

FIG. 5 shows the outer surface of a compression device according to the invention, such as that shown in FIG. 11. The band has a pocket sewn at a distal end of the band to serve as an aid when tightening the band. This is especially useful for persons who lack finger mobility, such as those persons suffering from arthritis, and cannot easily grasp bands between thumb and forefinger in order to pull on the band. The pocket helps the user to tighten a band in any compression device disclosed in this specification or, for that matter, any device or garment applied to the body. Embodiments include pockets positioned on one or a plurality of bands.

In the embodiment shown in FIGS. 5 and 11, the pocket is made of a hook material on the pocket's outward face. The pocket is attached by sewing to a band along the pocket's three edges with the fourth edge open, creating a space into which a portion of the hand or one or more fingers can be inserted.

FIG. 11 shows the pocket in use: the band 15 is wrapped around a body part L with one or more of the fingers of one hand being inserted in the pocket. The user can either push his or her fingers into the pocket 90 as shown in FIG. 11 or can hook his or her fingers into the pocket and pull (not shown) on the pocket to urge the distal region or end of the band in the desired direction. The end of the band with the pocket is tightened by pushing (or pulling) the fingers into the pocket and tucking the end 72 under the opposite end 77 of the band. At the same time, the opposite end 77 is pulled tight and wrapped over the pocket. The hook material of the pocket will help anchor the pocket to the inside face of the outer and opposite end of the band. A fastener, made of a hook material, is used to secure the end to the loop material of the outside surface of the band.

In another embodiment of the invention (not shown), the pocket can be made of a non-hook material, and the inward pressure of the band can be sufficient to anchor the end in place. As the hand is pulled out and away from the pocket, the opposing band end is brought down and attached to the outer surface of the band with a pocket using the fastener.

Opposing bands ends may be equipped with a pocket 90 that assists the user in tightening the garment and attaching the opposing band's hook surface to the outer surface of the garment. The garment is removed by separating the hook surfaces from the outer loop surfaces.

To facilitate handling the fabric during application to the body part and to prevent wrinkling of the fabric or slippage of the proximal (upper) end of the garment relative to the distal (lower) end, the fabric can be stiffened or reinforced longitudinally, such as by a strip, rod or other suitable means. In the therapeutic garment shown in FIG. 1 such reinforcement is provided by a longitudinal band 55 of Velcro-type fabric having an inner hook surface 60, which adheres to the outer loop surface 65 of the garment. The strip can be made of a high shear hook tape, such as Velcro P87 affixed along the vertical center line 70, i.e. longitudinal axis of the central region 10 of the garment to stiffen it and prevent wrinkling of the garment. See FIG. 2.

The therapeutic garment of this invention does not have to be custom-made to the body part because the fabric readily conforms to the body contour due to its inherent characteristics, such as light weight, flexibility and foldability, in contrast to heavier, thicker and more rigid materials used in the therapeutic device described in U.S. Pat. No. 4,215,687. In the therapeutic garment of the present invention, overlap of the bands is tolerated and is the basis of eliminating gaps and spaces in the compression applied to the body part.

Neoprene fabric is particularly advantageous in that stretch characteristics permit it to shape, mold, and conform to the body, while applying a near inelastic compression to the body part due to the fact that in tightening the bands the stretch limits are reached before the desired compression levels are achieved. The fabric can be oriented in the garment such that the greater stretch is in the longitudinal or vertical direction of the garment and the lesser stretch is in the transverse or horizontal direction of the garment. A preferred material for the garment is neoprene sheeting, such as that available from Perfectex Plus, Inc. of Huntington Beach, Calif. The advantages of neoprene are that it is thin, is available in wide sheets that have a moderate amount of stretch in one or both dimensions, retains its resiliency throughout repeated use, and is available laminated to other materials. For example a VELCRO-type loop material may be laminated on the surface of the neoprene to protect the neoprene, improve the comfort of wear, and provide a surface that will engage with hook materials. Other materials can also be used for this application, including laminates that use breathable open-cell foam instead of neoprene, provided they have the important properties described above.

The therapeutic compression garment shown in FIG. 1 can be made from an elastic fabric or an inelastic Velcro-loop type fabric or combination of both. Preferred embodiments have elastic bands and an inelastic central region. Any combination of elastic and inelastic materials that provides user comfort, conformance to the most curved portions of the limb, and ease of construction finds use in the invention. In certain embodiments, the central region 10 is wider proximally than distally to accommodate the larger circumference of proximal limb segments. The opposing limb compression bands are longer proximally than the limb compression bands distally located.

In FIGS. 1, 9, and 10, the opposing limb compression bands are separated from adjacent bands by spaces 12, wherein an oppositely situated band mates or fits with one or more opposite bands when it is wrappingly extended from the opposite lateral region. The bands may be angled relative to a proximal-distal longitudinal axis to completely encompass the limb with minimum overlap of the bands. The garment can be shortened longitudinally by cutting off upper or lower bands, one band at a time, horizontally to the opposing edge of the garment. The bands can also have varying widths 36, as can the length of the bands to accommodate any necking that occurs when elastic is being stretched. This can also be accounted for in sizing of spaces 12 in accompanying opposing bands. These spaces increase in width while the straps decrease in width while applying garment due to the characteristics of the semi-elastic material.

In FIG. 3, the therapeutic compression garment is made from an elastic fabric or an inelastic Velcro-loop type fabric or combination of both. The garment has a central region 10 for wrapping partially around the body part and a plurality of bands 15 connected to lateral regions 5, 6 of the central region and extending outwardly in opposite directions from lateral regions to encompass the body part. The bands 15 are defined by slits 13. Reduced band widths 31 are provided so that they register when wrappingly extended to accommodate the opposite band in a crossed overlapped relationship. Velcro-hook type surfaces 75 are carried at the ends or near the ends on the inner surfaces of each of the distal regions 80 of the bands.

The therapeutic compression garment of FIG. 5 can be made from an elastic Neoprene fabric or an inelastic Velcro-loop type fabric or combination of both. The garment has a central region 10 for wrapping partially around the body part and a plurality of bands 15 connected to the lateral regions of the central region and extending outwardly in opposite directions from to encompass the body part. The bands 15 are defined by slits 13 which are arranged generally perpendicular to the longitudinal axis 70 of the garment. The bands are arranged in a opposing paired relationship so that when wrappingly applied, one band of a pair completely overlaps the other. Velcro-hook type surfaces 75 are carried at the ends or near the ends on the inner surfaces of a distal region of one of the bands in each pair. In one embodiment, an opposite band in each pair may include a pocket 90 at or near the end of a distal region on the outer surface of the band. The user inserts fingers into the pocket to keep tension on the band while overlapping the other band of the pair and securing it to the outer loop surface 95 of the garment as shown in FIG. 6 and FIG. 11. FIG. 11 shows the pocket 90 in use. With fingers inserted into the pocket, the user wraps the band around body part L. The user can either push their fingers into the pocket 90 as shown in FIG. 11 or can hook their fingers into the pocket 90 and pull (not shown) on the pocket to urge the distal end 80 of the band in the desired direction. The distal end 80 of the band with the pocket is tightened by pushing (or pulling) the fingers into the pocket and tucking the end under the opposite distal end 100 of the band. At the same time the opposite distal end 100 is pulled tight and wrapped over the pocket. The pocket 90 can be made of hook and loop type hook material to help anchor the pocket to the inside of the outer opposite end of the band. A fastener 75 made of hook and loop type hook material is used to secure the end to the loop material of the outside surface 95 of the band. In addition to the pocket embodiment, there can be a Velcro-hook type fabric 75 to add additional support in securing the overlapped bands. The Velcro-hook type loop surfaces 75 would be positioned at or near the distal end of the band on the outer surface of a band opposing a band with a Velcro-hook type surface on the inner surface. When engaged, the Velcro-hook type surface of one band will attach to either the inner or outer loop surface of the opposing band as shown in FIG. 7.

The therapeutic compression garment of FIG. 8 (an exploded view) has a central region 10 made of a semi-elastic material such as neoprene and essentially inelastic bands 15 that can be made of a unitary piece of fabric with slits 13 defining the bands. The bands can also each be made separately. In either case the bands are attached to the lateral regions 7, 8 of the central region along the curved edges 110 which aid the garment in conforming to the limb shape, or can be attached using a hook and loop type material to the curved edges of the lateral regions of the central region 10. The edges of the lateral regions are cut to a curve that depends on the shape and size of the body part the garment is to fit. The bands are arranged in opposite paired relationship. Each of the bands has a region of reduced width 205 formed by recesses 37 in a proximal or distal edge of the band. The reduced width region is formed by material removal from one or both of the proximal and distal edges of the bands, for example from the proximal or upper edge of one member of the pair, and the distal or lower edge of the other. Accordingly, the bands can overlap and lay on top of each other without causing any increase in width at the point of crossing. Velcro-hook type surfaces are attached at or near the ends of the bands and are used to removably fasten the bands to loop type loop material positioned on a surface of the opposite band.

Compression Measuring System. The garment may also be equipped with a compression measuring system that utilizes the elasticity of the material to measure the amount of applied compression to ensure the garment is applied with gradient compression on the limb.

Guidance for structuring and using a system for measuring compression applied to a body part by a compression garment is disclosed in U.S. Pat. No. 6,338,723, herein incorporated by reference.

Figure 13:
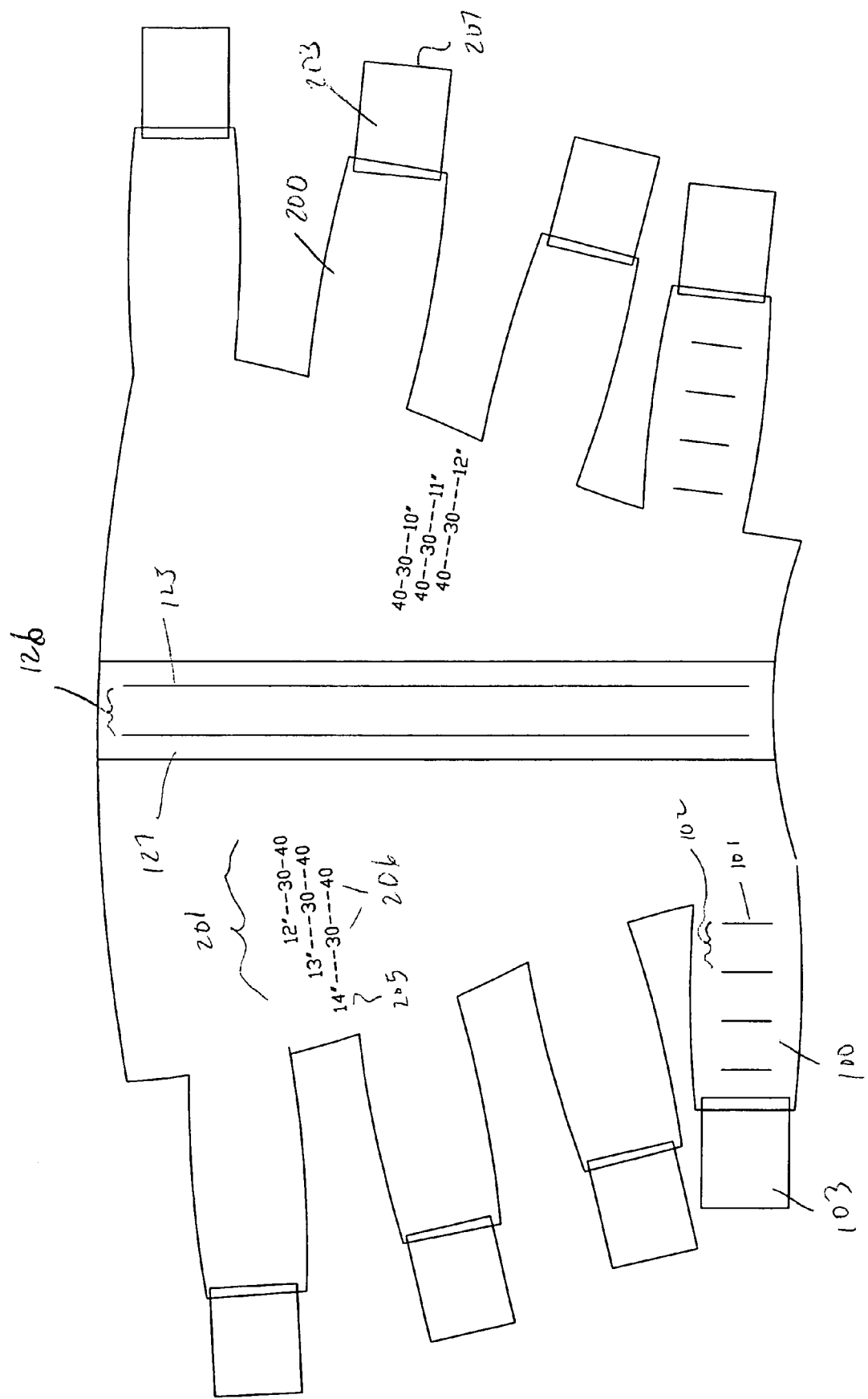
FIG. 13 is an embodiment of the device which has a examples of compression measuring systems on the outer surface.
Figure 14:
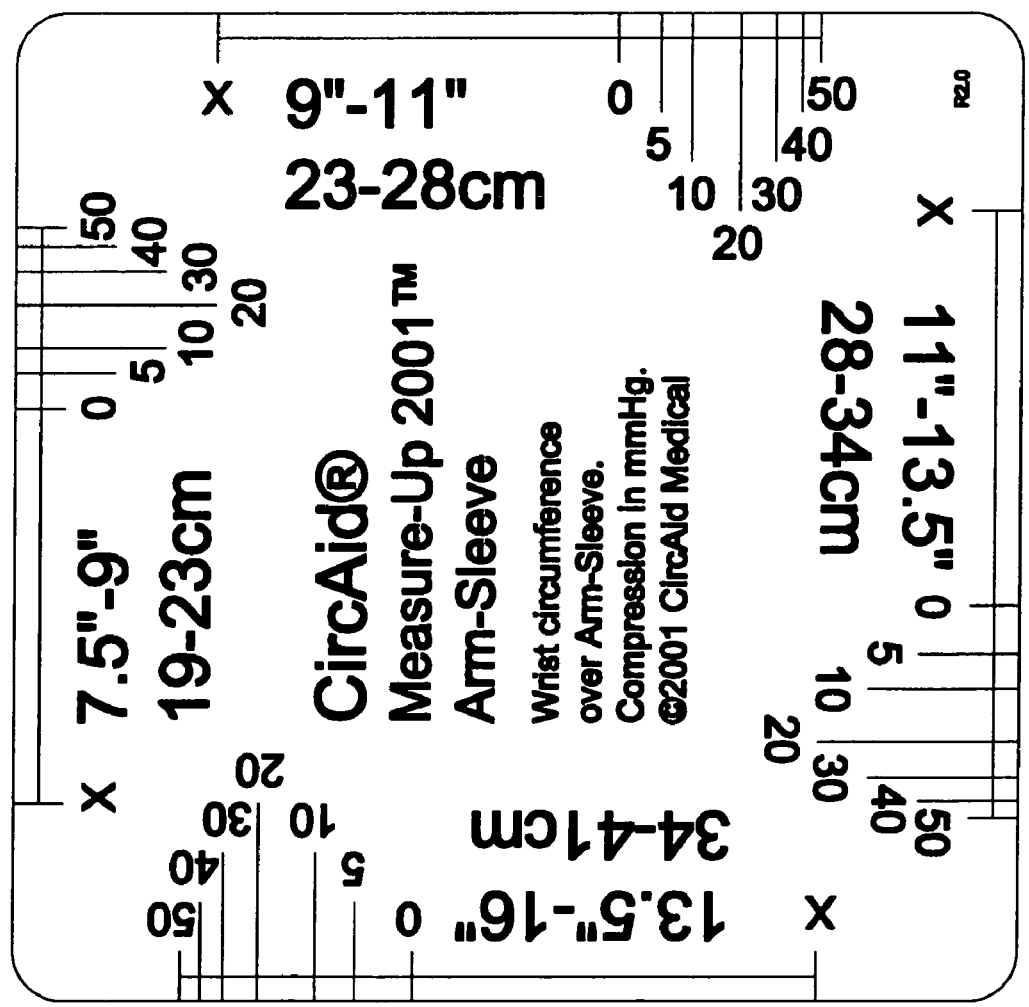
FIG. 14 is a calibrated measuring card.

One preferred embodiment of the compression device according to the invention provides a garment such as in FIG. 13 and a calibrated measuring scale or card (FIG. 14) that is used in combination with the bands to measure the stretch of elastic in the bands.

A portion of each band 100 is elastic or substantially elastic along the band's length or longitudinal axis, which is the axis along which tension is to be applied. Each band 100 could be made, of course, so that it is elastic along only a part of its length. Each band 100 has indicia 101 printed along its elastic length spaced by intervals 102. The interval 102 has a fixed or specified length when the band is not under tension, as in FIG. 13.

In the compression device shown in FIG. 13, the indicia can be two or more tick marks 101 spaced along the length of the band at intervals 102. Other embodiments of the indicia 101 could include dots, geometric shapes, symbols, patterns, text, or any other pattern spaced at intervals 102 along the elastic axis of the band 100 for measurement with a calibrated scale or card (as discussed below) upon application of the band or bands 100 to the body part and stretching of the band or bands 100. The intervals 101 are preferably at a uniform or specified distance from each other when the bands 100 are relaxed and not under tension, as shown in FIG. 13.

In an alternative embodiment, also shown in FIG. 13, the indicia 125 are two or more parallel lines spanning the length of the garment and spaced at intervals 126. These lines are on a portion 127 of the garment that is elastic along the entire length of the garment.

The measurement of elastic stretch or deformation along the elastic axis (depending upon the specific form of the embodiment), upon application of the garment in FIG. 13 to the body part, serves to accurately measure compression of the underlying body part. The interval 102 or 126 between successive indicia 101 or 125 will increase when the band 100 is tensioned and the elastic material of the band lengthens under tension. The user measures the distance between successive ones of the indicia 101 or 125 after application of the device to the body part. This distance is indicative of the tension in the elastic material of that part of the garment and, when the circumference of the body part is known, the compression applied by the device.

In the embodiment shown in FIG. 13, fasteners 103 made of hook material are attached to the ends of the bands 100. The bands 100 are wrapped around a body part, and the ends are held in place using the fasteners 103. After the user measures the circumference of the body part, a scale or card (FIG. 14) is used to determine the compression of the body part. As described below, the card is used to establish or verify equal or varying tension at different location on the garment as necessary. As an example, the natural distal-to-proximal increase of circumference of a body part such as a limb automatically yields a gradient of compression running up the limb for equal measured tension, without the user having to set a different target compression for different positions on the limb.

The compression device in FIG. 13 requires the use of means for measuring the distance 102, 126 between the indicia and means for correlating that distance to the amount of tension and/or, if the circumference of the body part is known, to the amount of compression of the body part surrounded by that portion of the garment. U.S. Pat. No. 6,338,723 (incorporated by reference), describes the structure and use of a card (see FIG. 14) having a plurality of edges with measurement scales for measuring the distance between the indicia 102 or 125 and means for correlating that distance to the amount of tension and/or, if the circumference of the body part is known, to the amount of compression of the body part surrounded by that portion of the garment. Indicia shown in FIGS. 13 and 14 correspond to units of actual compression values. Indicia could also correspond to units of force or arbitrary units enabling relative compression levels to be set.

In use, the band or bands 100 are applied directly around a body part or around other material that surrounds a body part. Tension on the bands 100 causes the elastic component of the device to stretch, increasing the intervals 102 or 126 between successive indicia 101 or 125. If the circumference of the body part under that portion of the garment is known, measuring the interval 102 or 126 of the indicia 101 or 125 provides a measure of compression under the garment at that point.

Compression devices according to the present invention include embodiments that do not require the use of a card or other such separate device in order to measure the compression. The means for measuring the stretch of the elastic component of a compression device and the means for correlating the stretch of the device to the compression that it provides are markings applied directly to the band, sleeve or garment of the compression device. The device itself therefore is used to measure the amount of compression that is provided to the limb or other body part.

FIG. 13 also depicts a compression device in which a portion of each band 200 is elastic or substantially elastic along at least a portion of its length. A fastener 203 is sewn to the end of the band and is preferably made of a hook material that will removeably attach to the loop material of the garment. Compression measurement indicia 201 are printed on a central region or lateral region of the exterior of the garment.

In this embodiment the indicia 201 each consist of one or more scales. Each scale is to be used for a specific circumference of the limb or body part that is to be compressed by the band 200. (Alternatively, each scale could be used for a particular compression that is to be achieved and the individual markings correspond to different circumferences, although this variation is not shown. Each scale 201 has a circumference marker 205 stating the circumference for which the scale 201 is calibrated. The circumference marker 205 is located at a distance from the edge or other specified portion of the band end, in a circumferential direction with respect to the body part that is equal to that circumference when the band 200 is not under tension. A series of marks 206 corresponds to various non-zero compression levels. The circumference marker 205 is also the zero compression mark for that circumference.

The band 200 is wrapped around the body part and the fastener 203 attaches the end 207 to the outer surface of the central region in the vicinity of the indicia 201. The user observes where the end 207 or other specified portion of the band 200 falls on the central region and thus which indicia 201 are contacted by the band end 207. If the circumference of the body part is known, the compression under the band 200 is easily determined by identifying the compression marking 206 associated with the scale for the circumference 205 that is closest to the measured circumference. The circumference can be either measured beforehand with a tape measure or similar device, or can be measured by the garment itself, by first wrapping the band 200 loosely around the limb without tension, and observing on which circumference marker 205 the band end 207 falls.

The position of the edge or other specified portion of the band 200 (and thus the marking it reaches) is a measure of the stretch of the band 200 and thus the tension it experiences. The tension is converted to compression by consideration of the circumference, the amount of overlap, and so forth as described in connection with the card shown in FIG. 14 (U.S. Pat. No. 6,338,723, herein incorporated by reference).

The indicia 201 could consist of pressure and/or circumference measurements themselves, or simplified indicators that could be referenced to a table that would give the compression based on the measured circumference of a body part and the indicator read from the band 200.

The therapeutic compression garment of FIG. 9 consists of a central region 10 made of an inelastic material and bands 15 made from a unitary piece of semi-elastic material with the spaces 12 defining the bands. Assembling the curved edges in the 110 aids the garment in conforming to the limb shape while, combined with the slight elasticity of the garment, prevents wrinkling and slippage of the proximal end of the garment relative to the distal end when applied to the body part. The elastic bands 15 may also be equipped with a measuring system that utilizes the elasticity of the material to measure the amount of applied compression to ensure the garment is applied with gradient compression on the limb. Velcro-hook type surfaces are attached at or near the ends of the bands and are used to removably fasten the bands to the outside hook and loop type loop material of the garment to apply the desired compression.

The therapeutic compression garment of FIG. 10 consists of a central region 10 made from multiple pieces of non-elastic material attached at curved edges 110 to create a central region that accommodates the limb shape. The pieces are stitched together (or otherwise assembled) in such a way as to form a central region with bands stitched or otherwise attached to the lateral regions of the central region. Those of skill in the art will understand that ways of joining multiple pieces of non-elastic material might be employed in place of stitching.

Darts may be cut into a single piece of fabric to create a central region that accommodates the limb shape. Darts or seams are sewn into the central region enable the garment to conform to the bent shape of an arm at the elbow, the leg at the knee, or another jointed body part. Also, by varying the width of the central region, the garment would be formed to taper, or otherwise vary in circumference, in order to conform to the shape of the body part. FIG. 8 shows a flat sheet of inelastic loop material with curved edges cut into it. FIG. 15 shows the assembly of the sheet into a central region 10. The darts 34 are closed by sewing the curved edges together, creating a bend or limb-accommodating contour in the finished garment so that when the lateral regions are wrapped around and towards each other, the central and lateral regions are biased into a three-dimensional curvature in order to fit the body part.

The present invention provides a further advantage of allowing the user to easily and rapidly adjust desired compression by adjusting the bands of garment as described above. In some forms of the present invention adjustment of the compression levels occurs at different portions of the limb longitudinally at the same time lending to an even faster adjustment time.

Longitudinal Slide Fastener Section Embodiments of the garment are equipped in the central region with a longitudinally extending slide fastener (FIG. 12) with which to separate portions of the central region. U.S. Pat. No. 6,109,267 (incorporated herein by reference) relates to a therapeutic compression device which includes a longitudinally extending splicing band or slide fastener which facilitates quick and easy removal of the device from the body or limb and quick and easy reapplication to the body or limb without the necessity of unthreading the adjusted compression bands. The longitudinal slide fastener provides the wearer quick removal and quick reapplication of the garment without detaching the bands which apply the desired compression.

A longitudinally extending slide fastener or zipper 120 extends at least the length of the central region 10 of the garment to facilitate removal and reapplication of the garment without unfastening the bands. In the therapeutic compression device shown in FIG. 12 for use on a leg, the runner 121 closes the slide fastener during its longitudinal movement from the upper end of the garment to the lower end of the garment and opens the slide fastener during its upward return movement. When the garment is applied to an arm, the direction of the closure of the runner 121 is reversed because starting the zipper closure requires both hands, and it would be virtually impossible to attach and start the zipper at the top of the arm.

Figure 12:
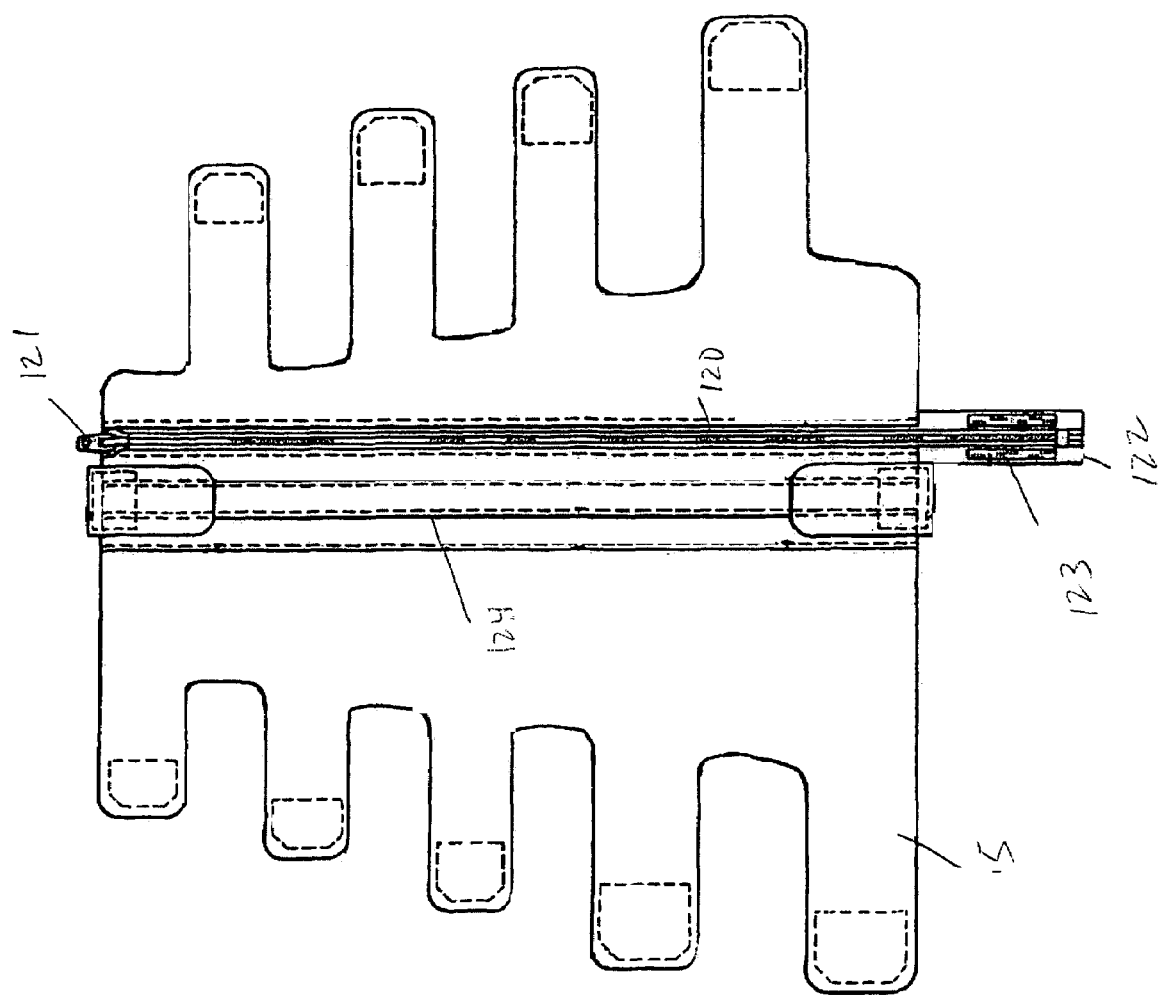
FIG. 12 is a view of the inner surface of an embodiment of the device in which a slide fastener is positioned in the central region.

In the preferred embodiment of the therapeutic compression garment shown in FIG. 12, the slide fastener extends at the upper end of the garment beyond the upper end of the garment to permit separation of the central region along its entire length while the separated portions of the central region remain connected by the extreme end of the extended portion of the slide fastener. The extended portion 122 shown in FIG. 12 permits the runner 121 to slide upwardly to open the slide fastener beyond the upper edge of the central region of the garment to facilitate removal of the garment from the body part and reapplication thereof. In this way, the garment can be removed and replaced by loosening and without unthreading the compression bands. The upward movement of the slide 121 is limited so that the separated portions of the central region of the garment remain connected by the end of the extended portion of the slide fastener. The extension 122 has a strip of hook tape 123 along each of its outer cloth edges to hold it against the outer loop surface of the garment in its folded down position.

A flap (not shown) may be provided to cover the slide fastener and the folded down zipper extension 122. If provided, the strips 123 of hook tape can be omitted. In the alternative, the outer surface of the flap can be provided with a Velcro-type loop surface and the extension and the hook surface strips can be folded over the flap and adhered thereto. The flap would also provide stiffening and wrinkling resistance which can be increased through the addition of a longitudinally extending rod 124 of stiff, flexible material (e.g. rubber).

The therapeutic compression garment shown in FIG. 12 equipped with a longitudinally extending stiffening rod and longitudinally extending slide fastener would preferably be worn such that the stiffening rod and slide fastener are located on the inside or outside of a limb to facilitate opening and closing the slide fastener and to prevent the stiffening rod from interfering with the bending of the knee or elbow. In this way, the stiffening rod flexes with the bending of the knee or elbow without undue wrinkling or distortion of the garment.

The garment also may include portions or a complete fabrication of a neoprene-type semi-elastic fabric for a smoother fit with better distribution of the applied compression. The garment may also consist of uniquely shaped pieces and seams, well known to those in the art of tailoring, such as but not restricted to darts, to better conform to the limb and better distribute the applied compression. Certain embodiments of the garment are formed from a flexible laminate material which has an inner padded layer of foam for comfort and an outer layer of hook and loop type material. Because of the ease of use and comfort of the garment, the invention provides the advantage of greater patient compliance.

Therapeutic Use

In therapeutic use, a method of the invention involves treating medical disorders, which require compression therapy. The method involves the step of applying to an indicated body part a garment of the invention whereby a compressive force or support is applied to the body part, such as the arm, foot, ankle, and leg on subjects (human or animal) suffering from disorders that require compression therapy. Such disorders include, but are not limited to, lymphedema, phlebitis, varicose veins, post-burn treatment, post-fracture and injury (including sports injury such as a pulled muscle) edema, stasis ulcers, obesity and circulatory disorders requiring application of compression devices.

Because human skin is elastic in nature, when such systems as the lymphatic or venous return systems fail to function properly, the limb or body part accumulates fluid and stretches to accommodate edema. Under normal operation, those systems would allow that fluid to circulate and not collect in those limbs or body parts and the skin would normally accommodate only the subtle changes by expanding or contracting. Use of non-elastic or substantially non-elastic compression garments of the present invention aid's the skin's strength, not allowing it to stretch and accumulate fluid. The fluid must then flow through the system from the compressive force of the non-elastic or substantially non-elastic compression device.

In addition, when a limb or body part is affected by poor circulation, the stagnated or poorly circulated fluid can manifest itself as ulcers. Use of compressive devices aids in that circulation. However, areas on such body parts or limbs at or near joints or concavities presents an obstacle to applying compressive devices because of the difficulties in applying and sustaining a uniform or gradient compression. The present invention overcomes this obstacles, in particular, by various embodiments which incorporate darts.

The invention has been shown in preferred forms and by way of example, and many variations and modifications can be made therein within the spirit of the invention. The invention, therefore, is not intended to be limited to any specified form or embodiment, except in so far as such limitations are expressly set forth in the claims.

What is claimed is:

1. A flat garment for applying compression to a body part, said garment comprising:
   a. a flat central region having inner and outer surfaces, said central region comprising substantially inelastic material, and lateral regions disposed on opposite sides of the central region;
   b. a plurality of bands extending from lateral margins disposed at opposite side edges of said opposite lateral regions, wherein the bands extending from the opposite lateral regions are juxtaposed to pass between one another and fasten onto the flat central region of the garment, each of said bands comprising
      i. a planar distal region
      ii. proximal and distal edges, wherein one or both edges comprise a curve or indentation,
      iii. inner and outer surfaces,
      iv. a fastener for detachably securing said distal region to a band extending from the opposite lateral region or to the opposite lateral or central region so as to encircle the body part and to draw the first lateral region toward the second longitudinal edge to stretch the central region and thereby provide a tension in the garment that will compress the body part.

2. The garment according to claim 1 wherein the central and lateral regions are biased into a three-dimensional curvature in order to fit the body part.

3. The garment of claim 2 wherein said opposing bands extend substantially perpendicular to a longitudinal axis of said central region, and said proximal and distal edges are substantially parallel to each other.

4. The garment of claim 1 wherein said plurality of bands are spaced-apart from each other and extend from each of said opposite lateral regions, wherein the positions from which adjacent bands extend from a lateral region are spaced apart.

5. The garment of claim 1 wherein each of said bands extend from a lateral region at an angle with respect to a longitudinal axis of the central region, and said angle is independently selected for each band.

6. The garment of claim 5 wherein
   at least one set of opposing bands extends substantially perpendicular to a longitudinal axis of said central region, and said proximal and distal edges are substantially parallel to each other; and
   at least one set of opposing bands extends at a non-normal angle to the longitudinal axis of the central region, in which the proximal and distal edges are substantially parallel to each other.

7. The garment of claim 1 for applying compression to a body part and having a system for measuring compression wherein said outer surface bears indicia printed thereon wherein measurement of a position of at least one of the indicia relative to a reference position on the outer surface provides a measurement of the stretch of the inelastic material.

8. The garment of claim 7 further comprising a card having a scale for measuring the separation of the position of the at least one indicia from the reference position and providing the compression level for the pre-measured circumference of the body part in order to determine the actual compression provided by the garment and adjusting the compression provided by the garment accordingly.

* * * * *